US009938559B2

(12) United States Patent
Kshirsagar et al.

(10) Patent No.: US 9,938,559 B2
(45) Date of Patent: Apr. 10, 2018

(54) BISMUTH-CONTAINING CONCENTRATION AGENTS FOR MICROORGANISMS

(71) Applicant: 3M INNOVATIVE PROPERTIES COMPANY, St. Paul, MN (US)

(72) Inventors: Manjiri T. Kshirsagar, Woodbury, MN (US); Evan Koon Lun Yuuji Hajime, Woodbury, MN (US); Andrew W. Rabins, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 70 days.

(21) Appl. No.: 14/391,904

(22) PCT Filed: Mar. 4, 2013

(86) PCT No.: PCT/US2013/028870
§ 371 (c)(1),
(2) Date: Oct. 10, 2014

(87) PCT Pub. No.: WO2013/184186
PCT Pub. Date: Dec. 12, 2013

(65) Prior Publication Data
US 2015/0079582 A1 Mar. 19, 2015

Related U.S. Application Data

(60) Provisional application No. 61/655,610, filed on Jun. 5, 2012.

(51) Int. Cl.
*C12Q 1/24* (2006.01)
*C12M 3/00* (2006.01)
*C12N 1/02* (2006.01)

(52) U.S. Cl.
CPC .................. *C12Q 1/24* (2013.01); *C12N 1/02* (2013.01)

(58) Field of Classification Search
None
See application file for complete search history.

(56) References Cited

U.S. PATENT DOCUMENTS

| | | | |
|---|---|---|---|
| 5,238,812 A | 8/1993 | Coulter | |
| 5,576,185 A | 11/1996 | Coulter | |
| 5,919,554 A * | 7/1999 | Watterson, III | A01N 25/34 428/192 |
| 7,112,272 B2 | 9/2006 | Hughes | |
| 7,112,280 B2 | 9/2006 | Hughes | |
| 7,169,304 B2 | 1/2007 | Hughes | |
| 7,422,868 B2 | 9/2008 | Fan | |
| 7,553,371 B2 * | 6/2009 | Dubrow | B01D 39/083 117/90 |
| 2008/0053922 A1 | 3/2008 | Honsinger, Jr. | |
| 2008/0229929 A1 * | 9/2008 | Marcoon | A62B 23/025 96/296 |
| 2010/0282083 A1 * | 11/2010 | Edwards | B01D 46/0028 95/285 |
| 2013/0224258 A1 * | 8/2013 | Baker | A01N 55/02 424/400 |

FOREIGN PATENT DOCUMENTS

| | | |
|---|---|---|
| EP | 0403048 | 12/1990 |
| WO | WO 2009-046183 | 4/2009 |
| WO | WO 2009-046191 | 4/2009 |
| WO | WO 2009-085357 | 7/2009 |
| WO | WO 2009-104890 | 8/2009 |
| WO | WO 2010-114725 | 10/2010 |
| WO | WO 2010-114727 | 10/2010 |
| WO | WO 2011-079038 | 6/2011 |

OTHER PUBLICATIONS

Sox et al., "Binding and Killing of Bacteria by Bismuth Subsalicylate," Antimicrobial Agents and Chemotherapy vol. 33, No. 12: 2075-2082 (1989).*
Gump et al., "Evidence that bismuth salts reduce invasion of epithelial cells by enteroinvasive bacteria," Med Microbiol Immunol 181: 131-143 (1992).*
Villareal, "Are Viruses Alive?" Scientific American (2008).*
Lambert et al., "The actions of bismuth in the treatment of Helicobacter pylori infection," Aliment Pharmacol Ther 11 (Suppl. 1): 27-33 (1997).*
Ford et al., "Adverse events with bismuth salts for Helicobacter pylori eradication: Systematic review and meta-analysis," World J Gastroenterol 14(48): 7361-7370 (2008).*
Keogan et al., "Current and Potential Applications of Bismuth-Based Drugs," Molecules 19: 15238-15297 (2014).*
Hernandez Delgadillo et al., "Zerovalent bismuth nanoparticles inhibit *Streptococcus mutans* growth and formation of biofilm," International Journal of Nanomedicine 7: 2109-2113 (2012).*
Ali Alharbi et al., "Bismuth-inhibitory effects on bacteria and stimulation of fungal growth," Saudi Journal of Biological Sciences 19: 147-150 (2012).*
Dellinger et al., "BiOCI Nanoparticles Synthesized in Lyotropic Liquid Crystal Nanoreactors," Scripta mater. 44: 1893-1897 (2001).*
Chen et al., "Fabrication of bismuth subcarbonate nanotube arrays from bismuth citrate," Chem. Commun. 2265-2267 (2006).*
JM Loveridge PLC, "Safety Data Sheet Bismuth Subcarbonate," Edition 1 (2002).*
Waldum et al., "A Bismuth Salt Inhibits Herpes Simplex Virus," Microbial Ecology in Health and Disease 10:13-15 (Year: 1998).*
Ali Alharbi et al., "Bismuth-inhibitory effects on bacteria and stimulation of fungal growth in vitro," Saudi Journal of Biological Sciences 19:147-150 (Year: 2012).*
Ward et al., "In Vitro Activities of Bismuth Salts Against Rotaviruses and Other Enteric Viruses," Antimicrobial Agents and Chemotherapy, vol. 27, No. 3: 306-308 (Year: 1985).*
Briand, "Bismuth Compounds and Preparations with Biological or Medicinal Relevance", Chemical Reviews, 1999, vol. 99, No. 9, pp. 2601-2657.
Manhart, "In Vitro Antimicrobial Activity of Bismuth Subsalicylate and Other Bismuth Salts", Reviews of Infectious Diseases, Jan.-Feb. 1990, vol. 12, No. 1, pp. S11-S15.

(Continued)

*Primary Examiner* — Janet L Andres
*Assistant Examiner* — M Franco G Salvoza
(74) *Attorney, Agent, or Firm* — Adrian L. Pishko; Stephen L. Crooks

(57) ABSTRACT

A bismuth-containing concentration agent for microorganisms is provided. Additionally, articles that include the concentration agent and methods of concentrating a microorganism using the concentration agent are provided.

11 Claims, No Drawings

(56) References Cited

OTHER PUBLICATIONS

Meyer, "Study of the Pharmacodynamic and Antimicrobial Action of Some Bismuth Salts", Microbiology Laboratory, Faculty of Pharmacy, Strasbourg, pp. 9-19 (1958).
Sox, "Binding and Killing of bacteria by bismuth subsalicylate", Antimicrobial Agents Chemotherapy, Dec. 1989, vol. 33, No. 12, pp. 2075-2082.
Stevens, "Bacterial Separation and Concentration from Complex Sample Matrices: A Review", Critical Reviews in Microbiology, 2004, vol. 30, No. 1, pp. 7-24.
International Search Report for PCT International Application No. PCT/US2013/028870 dated Jun. 6, 2013, 3 pages.

\* cited by examiner

BISMUTH-CONTAINING CONCENTRATION AGENTS FOR MICROORGANISMS

CROSS REFERENCE TO RELATED APPLICATIONS

This application is a national stage filing under 35 U.S.C. 371 of PCT/US2013/028870, filed Mar. 4, 2013, which claims priority to Provisional Application No. 61/655,610, filed Jun. 5, 2012, the disclosure of which is incorporated by reference in its/their entirety herein.

FIELD

Concentration agents for microorganisms, articles that include the concentration agents, and processes for concentrating microorganisms are provided.

BACKGROUND

Infections resulting from microorganism contamination are a growing concern. Thus, it is often desirable or necessary to assay for the presence of microorganisms in various clinical, food, environmental, and other types of samples to identify and/or to quantify the microorganisms that are present. The ability to detect the presence of a particular microorganism is often dependent on the concentration of the microorganism in the sample being analyzed.

Various physical concentration methods such as, for example, filtration, chromatography, centrifugation, and gravitational settling have also been utilized for non-specific capture of various microorganisms. Such non-specific concentration methods have varied in speed, cost (at least some requiring expensive equipment, materials, and/or trained technicians), sample requirements (for example, sample nature and/or volume limitations), space requirements, ease of use (at least some requiring complicated multi-step processes), suitability for on-site use, and/or effectiveness. Some of these physical concentration methods have additionally used inorganic materials such as various metal hydroxides and/or metal oxides as concentration agents for the microorganisms, such as, for example, those described in PCT International Publication Numbers WO 2009/046183 A1 (Kshirsagar), WO 2009/046191 A2 (Kshirsagar), WO 2009/085357 A2 (Kshirsagar), WO 2010/114725 A1 (Kshirsagar), WO 2010/114727 A1 (Kshirsagar), and WO 2011/079038 (Kshirsagar).

SUMMARY

New concentration agents suitable for the non-specific concentration of microorganisms (for example, strains of bacteria, fungi, yeasts, protozoan, viruses, and bacterial endospores) are desired and are provided herein. Additionally, articles that include the concentration agent and methods of concentrating a microorganism using the concentration agent are provided. The concentration agent contains bismuth.

The concentration agents can be used to increase the concentration of microorganisms such as pathogenic organisms to a level suitable for detection. The concentration agents provide a rapid, simple (i.e., involving no complex equipment or procedures) method of concentrating various microorganisms. The concentration agents can be used effectively under a variety of conditions, such as with a variety of types of sample matrices, a variety of different bacterial loads, and a variety of different sample volumes.

In a first aspect, a process for concentrating microorganisms is provided. The process includes providing a concentration agent that contains a bismuth-containing compound, wherein the bismuth-containing material is any of bismuth oxide, bismuth carbonate, bismuth oxycarbonate, bismuth oxychloride, or a mixture thereof. The process further includes providing a fluid sample that contains the microorganism and contacting the concentration agent with the fluid sample. The process still further includes binding the microorganism to the concentration agent to form a bound microorganism, wherein the bound microorganism is living.

In a second aspect, an article is provided that includes a concentration agent and a microorganism bound to the concentration agent. The concentration agent contains a bismuth-containing compound, wherein the bismuth-containing material is any of bismuth oxide, bismuth carbonate, bismuth oxycarbonate, bismuth oxychloride, or a mixture thereof.

In a third aspect, an article is provided that includes a concentration agent and a porous matrix. The concentration agent contains a bismuth-containing compound, wherein the bismuth-containing material is any of bismuth oxide, bismuth carbonate, bismuth oxycarbonate, bismuth oxychloride, or a mixture thereof. The concentration agent is distributed on a surface of the porous matrix, throughout the porous matrix, or a combination thereof. In some embodiments, the porous matrix includes nonwoven fibers and an optional polymeric binder.

DETAILED DESCRIPTION

A concentration agent, articles that include the concentration agent, and processes of concentrating a microorganism using the concentration agent are provided. More specifically, the concentration agent contains a bismuth-containing material. The concentration agent can be used to concentrate or capture microorganisms. The concentration agent is generally not specific to any particular strain, species, or type of microorganism and can therefore be used for the concentration of a general population of microorganisms in a sample. Specific microorganisms can be detected from among the captured microorganism population using any known detection method directed to the specific microorganism.

The terms "a", "an", "the", "at least one" are used interchangeably.

The term "and/or" means one or both of the listed elements. For example, A and/or B means, A alone, B alone, or both A and B.

The term "comprises" and variations thereof do not have a limiting meaning when used in the description and claims.

A numerical range includes the endpoints of the range and all numbers within the range.

In some embodiments, the bismuth-containing material is any of bismuth oxide ("$Bi_2O_3$"), bismuth carbonate ("$Bi_2(CO_3)_3$"), bismuth oxycarbonate ("$Bi_2O_2(CO_3)$"), bismuth oxychloride ("BiOCl"), or a mixture thereof.

In some embodiments, the bismuth-containing material is hydrated. In some embodiments, the bismuth-containing compound is anhydrous.

In some embodiments, the concentration agent does not contain bismuth oxide. In other embodiments, the concentration agent includes up to 20 weight percent bismuth oxide. For example, the concentration agent can contain up to 10 weight percent, up to 5 weight percent, up to 2 weight percent, or even up to 1 weight percent bismuth oxide.

The concentration agent typically includes particles. Stated differently, the bismuth-containing material in the concentration agent is often in the form of a plurality of particles. Although these particles can have any desired size, the average size (i.e., the average size of the largest dimension) of the particles is typically no greater than 100 micrometers, no greater than 75 micrometers, no greater than 50 micrometers, no greater than 40 micrometers, no greater than 30 micrometers, no greater than 20 micrometers, or even no greater than 10 micrometers. The particles typically have an average particle diameter that is greater than 1 micrometer, greater than 2 micrometers, or even greater than 5 micrometers. For example, the average diameter of the particles can be in a range of 1 to 100 micrometers, 1 to 75 micrometers, 1 to 50 micrometers, 1 to 20 micrometers, or even 1 to 10 micrometers.

Microorganisms can be bound to the concentration agent. Stated differently, the bismuth-containing material in the concentration agent can be used to capture, isolate, separate, remove, or concentrate microorganisms from a fluid sample. Any fluid sample of interest can be used that potentially includes a microorganism. The fluid sample can be a liquid, a dispersion or suspension of solids in a liquid, or a dispersion or suspension of a first liquid in a second liquid. The fluid sample can be used directly, can be concentrated (for example, by centrifugation or evaporation), or can be diluted (for example, by addition of a buffer such as a pH buffer solution). Samples that are in the form of a solid or a semi-solid can be extracted (for example, by washing or rinsing with a fluid) or can be suspended or dispersed in a fluid. Samples can be taken from surfaces by swabbing and/or rinsing with a fluid. The samples can include, but are not limited to, biological samples, environmental samples, food samples, feed samples, laboratory sample, and industrial samples.

Some specific food samples that can be used either directly or indirectly after treatment with a fluid phase include, but are not limited to, fresh produce, ground meat, dairy products, juices, beverages, and the like. Food samples may also result from inspection of food processing equipment, food handling equipment, food preparation areas, and the like. Some specific biological fluids that can be used either directly or indirectly after treatment with a fluid phase include, but are not limited to, whole bloods or a component of whole blood (for example, plasma, a platelet-enriched blood fraction, a platelet concentrate, and packed red blood cells), cell preparations (for example, dispersed tissue, bone marrow aspirate, and vertebral body bone marrow), cell suspensions, urine, saliva, lung fluid, cerebral fluid, wound exudates, wound biopsy samples, ocular fluid, spinal fluid, and lysed preparations. Environmental samples that can be used either directly or indirectly after treatment with a fluid phase include, but are not limited to, potable water, ground water, soil samples, and industrial waste samples. Still other industrial samples are those associated with various bioprocesses or pharmaceutical formulations.

The fluid sample and the concentration agent are brought into contact. The concentration agent can be added to the fluid sample or the fluid sample can be added to the concentration agent. Any suitable amount of the fluid sample and the concentration agent can be used. The volume of the fluid sample is often dependent on the particular application. When the fluid sample is related to a diagnostic or research application, the volume may be in a microliter range (for example, 1 microliter to 1000 microliters). When the fluid sample is related to food pathogen testing or for potable water testing, the volume may be in the milliliter to liter range (for example, 1 milliliter to 10 liters or more). When the fluid sample is related to an industrial application, the volume may be several hundred liters or more. The amount of the concentration agent needed relative to the volume of the fluid sample can be readily determined by those skilled in the art. In some applications, 1 to 10 milligrams of concentration agent per milliliter of sample can be useful.

In many embodiments, at least a portion of the concentration agent can be suspended or dispersed in the fluid sample. For example, a spatula or dipstick or other article bearing the concentration agent can be immersed into a fluid sample. In other examples, a fluid sample can be poured onto a film bearing the concentration agent or a fluid sample can be added to a tube or well containing the concentration agent. In still other examples, the concentration agent and the fluid sample are combined (using any order of addition) in any of a variety of containers. These containers can optionally be capped, closed, or sealed such as capped test tubes and capped bottles or jars. The containers, if desired, can be sterilized prior to addition of the fluid sample.

Contact between the concentration agent and the fluid sample can be enhanced by mixing (for example, stirring, agitation, shaking, or rocking) such that the concentration agent is exposed to a substantial portion of the fluid sample. For small fluid samples such as those having a volume less than or equal to 1 milliliter, mixing methods such as forming a vortex can be used as described, for example, in U.S. Pat. No. 5,238,812 (Coulter et al.). For larger volumes, such as those ranging from 1 milliliter to 10 liters, mixing can be achieved by gently tumbling the concentration agent and the fluid sample in an "end over end" fashion as described, for example, in U.S. Pat. No. 5,576,185 (Coulter et al.). Contacting can be carried out for any desired time period. For fluid samples having volumes of about 100 milliliters or less, the contact time can be up to 60 minutes, up to 45 minutes, up to 30 minutes, up to 20 minutes, up to 10 minutes, or even up to 5 minutes. The contact time for such fluid samples is often at least 5 seconds, at least 10 seconds, at least 15 seconds, at least 30 seconds, or even at least 1 minute.

If desired, one or more additives can be added to the mixture of fluid sample and concentration agent. Suitable additives include, but are not limited to, lysis reagents, bioluminescence assay reagents, microbial growth media, buffers (for example, to disperse or extract a solid sample), microbial staining reagents, washing buffers (for example, to wash away unbound material), elution agents (for example, serum albumin), surfactants, and mechanical abrasion/elution agents (for example, glass beads).

While the fluid sample is in contact with the concentration agent, microorganisms present in the fluid sample can become bound to the concentration agent. The bound microorganism (i.e., the microorganism bound to the concentration agent) can be separated from the residual fluid sample. In some embodiments, such separation can be accomplished by relying, at least in part, upon gravitational settling. For example, the bound microorganism can settle over of period of time up to 60 minutes, up to 45 minutes, up to 30 minutes, up to 15 minutes, up to 10 minutes, or even up to 5 minutes. In other embodiments, such separation can be accomplished by techniques such as centrifugation. In either of these embodiments, the supernatant can be removed by decanting, siphoning, filtration, or other methods known in the art. The bound microorganism can remain at the bottom of the container or vessel used during the separation step. Alternatively, the bound microorganism can be on filter media.

In other method of contacting the fluid sample with the concentration agent, the concentration agent is part of a concentration device that also includes a porous matrix. The concentration agent in these concentration devices is in the form of a plurality of particles that are distributed on a surface of the porous matrix, throughout the porous matrix, or a combination thereof. Any suitable porous matrix can be used.

In some embodiments of the concentration device, the porous matrix is polymeric and is formed using sinterable polymeric particles. That is, the concentration device includes (a) a porous matrix of sintered polymeric particles and (b) a plurality of concentration agent particles that include bismuth-containing material. The concentration agent particles are distributed on a surface of the porous matrix, throughout the porous matrix, or a combination thereof.

To form this concentration device, the sinterable polymeric particles and concentration agent particles are mixed together and heated to a temperature sufficient to soften the polymeric particles. Upon cooling, the softened polymeric materials fuse together to form a porous matrix of sintered polymeric particles. The resulting concentration device is often in the form of a solid or self-supporting porous matrix with the concentration agent embedded within the porous matrix, on a surface of the porous matrix, or both. The concentration device can have a complex pore structure (for example, a tortuous path of pores throughout the porous matrix) and can have good mechanical strength.

Polymers that are capable of being sintered when in particulate form include various thermoplastic polymers. Thermoplastic polymers with relatively high viscosities and relatively low melt flow rates can facilitate particle shape retention during the sintering process (i.e., if the particle shape is not retained, a body with low or no porosity can result).

Useful thermoplastic polymers include, but are not limited to, polyolefins (including olefin homopolymers and copolymers, as well as copolymers of olefins and other vinyl monomers), polysulfones, polyethersulfones, polyphenylene sulfide, and the like, and combinations thereof. Representative examples of useful polymers include ethylene vinyl acetate (EVA) polymers, ethylene methyl acrylate (EMA) polymers, polyethylenes (including, for example, low density polyethylene (LDPE), linear low density polyethylene (LLDPE), high density polyethylene (HDPE), and ultra-high molecular weight polyethylene (UHMWPE)), polypropylenes, ethylene-propylene rubbers, ethylene-propylene-diene rubbers, polystyrene, poly(1-butene), poly(2-butene), poly(1-pentene), poly(2-pentene), poly(3-methyl-1-pentene), poly(4-methyl-1-pentene), 1,2-poly-1,3-butadiene, 1,4-poly-1,3-butadiene, polyisoprene, polychloroprene, poly(vinyl acetate), poly(vinylidene chloride), poly(vinylidene fluoride), poly(tetrafluoroethylene), and the like, and combinations thereof.

In some more specific concentration devices, the thermoplastic polymer used to form the polymeric porous matrix includes polyethylene such as ultra-high molecular weight polyethylene (UHMWPE). Examples ultra-high molecular weight polyethylene are those having a weight average molecular weight of at least about 750,000 grams/mole, at least 1,000,000 grams/mole, at least 2,000,000 grams/mole, or even at least 3,000,000 grams/mole.

The sinterable polymers can have a wide range of particle sizes depending upon the pore (for example, hole, depression, or, preferably, channel) sizes desired in the sintered, polymeric porous matrix. Finer particles can result in finer pore sizes in the porous matrix. Generally, the polymer particles can be micro-particles having an average size (i.e., diameter of the longest dimension) in a range of 1 to 1000 micrometers. For example, the average particle size can be in a range of 1 to 750 micrometers, in a range of 1 to 500 micrometers, in a range of 1 to 300 micrometers, in a range of 5 to 300 micrometers, in a range of 1 to 200 micrometers, in a range of 5 to 200 micrometers, in a range of 10 to 200 micrometers, in a range of 50 to 200 micrometers, or even in a range of 100 to 200 micrometers. The resulting pores can be in the micrometer range or less. If desired, the porosity of the porous matrix can also be varied or controlled by using blends of higher and lower melt flow rate thermoplastic polymers.

The thermoplastic polymer particles and the concentration agent particles (and any optional additives, such as wetting agents or surfactants) can be combined and mechanically blended (for example, using commercial mixing equipment) to form a mixture. The mixture is typically blended until it is homogeneous. Generally, the particulate concentration agent can be present in the mixture at a concentration of up to 90 weight percent based on a total weight of solids in the mixture. The solids typically include the polymeric particles, the concentration agent particles, and any additional solids associated with optional additives. If higher amounts of the concentration agent are used, the concentration device may contain an insufficient amount of polymeric material to form a porous matrix. The concentration agent can be present, for example, in an amount up to 85 weight percent, up to 80 weight percent, up to 75 weight percent, or even up to 70 weight percent based on the total weight of solids in the mixture. The amount of the concentration agent is typically at least 5 weight percent based on a total weight of solids in the mixture. If the amount of the concentration agent is lower, the capture efficiency of microorganisms by the concentration agent may be insufficiently low. The amount of the concentration agent is often at least 10 weight percent, at least 20 weight percent, at least 30 weight percent, at least 40 weight percent, or even at least 50 weight percent based on the total weight of the solids in the mixture.

Some example concentration devices contain 5 to 90 weight percent concentration agent particles and 10 to 95 weight percent polymeric particles based on the total weight of solids in the mixture. For example, the concentration devices can contain 10 to 80 weight percent concentration agent particles and 20 to 90 weight percent polymeric particles, 20 to 80 weight percent concentration agent particles and 20 to 80 weight percent polymeric particles, 40 to 80 weight percent concentration agent particles and 20 to 60 weight percent polymeric particles, or even 10 to 50 weight percent concentration agent particles and 50 to 90 weight percent polymeric particles. Conventional additives (for example, wetting agents, surfactants, or the like) can be included in the mixture in small amounts (for example, up to 5 weight percent), if desired.

The resulting mixture can be placed in a mold or other suitable container or substrate. Useful molds, which can have a single cavity or multiple cavities, can be fabricated from carbon steel, stainless steel, brass, aluminum, titanium, nickel, or the like. The cavities can be of essentially any desired shape, provided that the sintered, polymeric porous matrix can be removed from the mold after processing is completed. The molds can be filled using commercial powder handling and/or vibratory equipment.

Thermal processing to sinter the polymeric particles can be carried out by introducing heat to the mold (for example, through electrical resistance heating, electrical induction heating, or steam heating). The mold can be heated to a temperature sufficient to sinter the polymer (for example, by heating to a temperature slightly below the melting point of the polymer). The temperature is often in a range of 90° C. to 200° C. or higher depending on the molecular weight of the polymeric particles. For example, the temperature can be in a range of 100° C. to 200° C., in a range of 120° C. to 200° C., in a range of 100° C. to 180° C., or even in a range of 120° C. to 180° C. Optionally, pressure can be applied to the mixture during the heating process. After thermal processing, the mold can be allowed to cool to ambient temperature (for example, a temperature in a range of 20° C. to 25° C.) naturally or through use of essentially any convenient cooling method or device.

An example concentration device can be prepared using the polymer particles and processing methods described in U.S. Pat. No. 7,112,272 (Hughes et al.), U.S. Pat. No. 7,112,280 (Hughes et al.), and U.S. Pat. No. 7,169,304 (Hughes et al.). Two different types of ultra-high molecular weight polyethylene (UHMWPE) particles can be blended together, one being "popcorn-shaped" with surface convolutions and the other being substantially spherical. Example "popcorn-shaped" and spherical UHMWPEs are available from Ticona (a division of Celanese, headquartered in Frankfurt, Germany) as PMX CF-1 (having a bulk density of 0.25-0.30 grams/cubic centimeter and an average diameter of about 30 to 40 micrometers, with a range from about 10 micrometers to about 100 micrometers) and PMX CF-2 (having a bulk density of 0.40-0.48 grams/cubic centimeter and an average diameter of about 55 to 65 micrometers, with a range from about 10 micrometers to about 180 micrometers), respectively. UHMWPEs from other manufacturers having comparable morphologies, bulk densities, and particle sizes and having weight average molecular weights in the range of about 750,000 grams/mole to about 3,000,000 grams/mole can also be utilized. The two types of UHMWPE particles can be selected to be of the same or different molecular weight. In one more particular example, both types of particles have a similar molecular weight within the stated range; for example, both types of particles can have a weight average molecular weight close to 3,000,000 grams/mole). The two types of UHMWPE particles can be combined in varying relative amounts (for example, equal amounts) and then further combined with concentration agent in the ratios described above. Either type of UHMWPE can be used in lesser amount than the other, or can even be omitted from the mixture, depending upon the desired characteristics of the concentration device.

In other embodiments of a concentration device, the porous matrix is fibrous and nonwoven. That is, the concentration device includes (a) a fibrous, nonwoven porous matrix and (b) a plurality of concentration agent particles that include bismuth-containing material. The concentration agent particles are distributed on a surface of the porous matrix, throughout the porous matrix, or a combination thereof.

Such concentration devices can be prepared by essentially any process that is capable of providing a fibrous nonwoven porous matrix having the concentration agent particles enmeshed therein. This type of porous matrix is typically a web or medium that contains interlaid fibers in a form that is not woven or knitted fabric. Useful processes for preparing the fibrous, nonwoven porous matrix include, but are not limited to, air laying techniques, spunlaid techniques such as melt blowing or spunbonding, carding, wetlaying, and combinations thereof. In some applications, it may be preferable to prepare the fibrous nonwoven matrix by spunlaid or wetlaid techniques.

Fibers suitable for use in preparing the fibrous, nonwoven porous matrix of the concentration device are usually pulpable or extrudable fibers such as those that are stable to radiation and/or to a variety of solvents. Useful fibers include polymeric fibers, inorganic fibers, and combinations thereof. In many embodiments, the fibers include polymeric fibers and often include a plurality of different types of polymeric fibers. For example, at least some of the polymeric fibers can be selected to exhibit a degree of hydrophilicity.

Suitable polymeric fibers include those made from natural polymers (those derived from animal or vegetable sources) and/or synthetic polymers, including thermoplastic and solvent-dispersible polymers. Useful polymers include wool; silk; cellulosic polymers (for example, cellulose, cellulose derivatives such as rayon, and the like); fluorinated polymers (for example, poly(vinyl fluoride), poly(vinylidene fluoride), copolymers of vinylidene fluoride such as poly (vinylidene fluoride-co-hexafluoropropylene), copolymers of chlorotrifluoroethylene such as poly(ethylene-co-chlorotrifluoroethylene), and the like); chlorinated polymers; polyolefins (for example, poly(ethylene), poly(propylene), poly (1-butene), copolymers of ethylene and propylene, alpha olefin copolymers such as copolymers of ethylene or propylene with 1-butene, 1-hexene, 1-octene, and 1-decene, poly(ethylene-co-1-butene), poly(ethylene-co-1-butene-co-1-hexene), and the like); poly(isoprenes); poly(butadienes); polyamides (for example, nylon 6, nylon 6,6, nylon 6,12, poly(iminoadipoyliminohexamethylene), poly(iminoadipoyliminodecamethylene), polycaprolactam, and the like); polyimides (for example, poly(pyromellitimide) and the like); polyethers; poly(ether sulfones) (for example, poly (diphenylether sulfone), poly(diphenylsulfone-co-diphenylene oxide sulfone), and the like); poly(sulfones); poly (vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly(phosphazenes); poly(vinyl esters); poly(vinyl ethers); poly(vinyl alcohols); polyaramids (for example, para-aramids such as poly(paraphenylene terephthalamide) and fibers sold under the trade designation "KEVLAR" by DuPont Co., Wilmington, Del., pulps of which are commercially available in various grades based on the length of the fibers that make up the pulp such as, for example, "KEVLAR 1F306" and "KEVLAR 1F694", both of which include aramid fibers that are at least 4 mm in length; and the like); poly(carbonates); and the like; and combinations thereof. In some specific examples, the polymeric fibers include polyamides, polyolefins, polysulfones, and combinations thereof. An even more specific example includes nylon, poly(ethylene), and combinations thereof.

Suitable inorganic fibers include those that contain at least one inorganic material selected from glasses, ceramics, and combinations thereof. Useful inorganic fibers include, for example, fiberglass (for example, E-glass, S-glass, and the like), ceramic fibers (for example, fibers made of metal oxides (such as alumina), silicon carbide, boron nitride, boron carbide, and the like), and combinations thereof. Useful ceramic fibers can be at least partially crystalline (exhibiting a discernible X-ray powder diffraction pattern or containing both crystalline and amorphous (glass) phases). In some applications, the inorganic fibers include fiberglass and combinations thereof.

The fibers used to form the fibrous nonwoven porous matrix can be of a length and diameter that can provide a porous matrix having sufficient structural integrity and sufficient porosity for a particular application (for example, for a particular type of sample matrix). For example, the fiber lengths are often at least about 0.5 millimeter, at least 1 millimeter, at least 2 millimeters, at least 3 millimeters, at least 4 millimeters, at least 6 millimeters, at least 8 millimeters, at least 10 millimeters, at least 15 millimeters, at least 20 millimeters, at least 25 millimeters, or even at least 30 millimeters. The diameter of the fibers can be, for example, at least 10 micrometers, at least 20 micrometers, at least 40 micrometers, or even at least 60 micrometers. The fiber lengths and diameters will vary depending upon factors such as the nature of the fiber and the type of application.

To facilitate entrapment of the concentration agent particles and/or to ensure a high surface area, the fibers used to form the fibrous nonwoven porous matrix often contain at least one fibrillated fiber (for example, in the form of a main fiber surrounded by many smaller attached fibrils). The main fiber generally can have a length in the range of 0.5 millimeter to 5 millimeters and a diameter in a range of 1 micrometer to 20 micrometers. The fibrils typically can have a sub-micrometer diameter.

The fibrous nonwoven porous matrix can contain a plurality of different types of fibers. In some embodiments, the porous matrix can be formed using two, three, four, or even more different types of fibers. For example, a nylon fiber can be added for strength and integrity, while fibrillated polyethylene can be added for entrapment of the particulates. If fibrillated and non-fibrillated fibers are used in combination, the weight ratio of fibrillated fibers to non-fibrillated fibers is often at least 1:2, at least 1:1, at least 2:1, at least 3:1, at least 5:1, or even at least 8:1.

The concentration devices often contain at least 10 weight percent fibers based on a total weight of solids in the concentration device (for example, fiber, polymeric binder, and concentration agent). If the amount of fibers included is less than this amount, the concentration device may not have sufficient porosity. Some concentration devices contain at least 15 weight percent, at least 20 weight percent, or even at least 25 weight percent fibers. The fibrous porous matrix often contains up to 95 weight percent fibers based on a total weight of solids. If the amount of fiber is greater than this amount, there may be an insufficient amount of the concentration agent present to capture microorganisms when contacted with a fluid sample. Some example concentration devices contain up to 90 weight percent, 80 weight percent, up to 70 weight percent, up to 60 weight percent, or even up to 50 weight percent fibers based on the total weight of solids.

The fibrous, nonwoven porous matrix often further contains at least one polymeric binder. Suitable polymeric binders include natural and synthetic polymeric materials that are relatively inert (exhibiting little or no chemical interaction with either the fibers or the concentration agent particles). Useful polymeric binders include polymeric resins (for example, in the form of powders and latexes), polymeric binder fibers, and the like, and combinations thereof.

Suitable polymeric resins for used in the fibrous, nonwoven porous matrix include, but are not limited to, natural rubbers, neoprene, styrene-butadiene copolymers, acrylate resins, polyvinyl chloride, polyvinyl acetate, and combinations thereof. In many embodiments, the polymeric resin includes acrylate resins.

Suitable polymeric binder fibers include adhesive-only type fibers and bi-component fibers. Example adhesive-only type fibers include those commercially available under the trade designation KODEL (for example, KODEL 43UD) from Eastman Chemical Products (Kingsport, Tenn., USA). Bi-component fibers can be, for example, side-by-side forms, sheath-core forms, or the like. An example side-by-side bi-component fiber is the polyolefin thermally bonded bi-component fiber that is commercially available from Chisso Corporation (Osaka, Japan) under the trade designation CHISSO (for example, CHISSO ES). An example sheath-core bi-component fiber is commercially available from Unitika Ltd. (Osaka, Japan) under the trade designation MELTY (for example, MELTY 4080). This fiber has a polyester core and a poly(ethylene) sheath. Another commercially available sheath-core bi-component fiber that is made of ethyl vinyl acetate (sheath) and polypropylene (core) is available from Minifibers (Johnson City, Tenn.).

Regardless of the type of polymeric binder used, the amount of binder in the resulting concentration device (in dry form) is often in a range of 0.5 to 10 weight percent based on a total weight of solids in the concentration device (for example, fiber, polymeric binder, and concentration agent). Such amounts of polymeric binder generally can provide the fibrous, nonwoven porous matrix with sufficient integrity for use in many applications, while not significantly coating the concentration agent particles. For example, the amount of polymeric binder can be in a range of 1 to 8 weight percent, 1 to 6 weight percent, 1 to 5 weight percent, 1 to 4 weight percent, 2 to 8 weight percent, or even 3 to 7 weight percent based on a total weight of solids in the concentration device.

Preferably, the polymeric binder does not substantially adhere to the concentration agent particles. In other words, when the concentration device is examined by scanning electron microscopy, less than 5 percent of a total surface area of the concentration agent particle is covered with polymeric binder. For example, less than 4 percent, less than 3 percent, less than 2 percent, or even less than 1 percent of the total surface area of the concentration agent is covered with the polymeric binder.

This type of concentration device can be prepared by a process that includes (a) providing a plurality of the above-described fibers; (b) providing a plurality of the above-described concentration agent particles; and (c) forming at least a portion of the plurality of fibers into a porous fibrous nonwoven matrix having at least a portion of the plurality of concentration agent particles enmeshed therein. As mentioned above, the forming can be carried out by essentially any process that is capable of providing a fibrous nonwoven matrix having the concentration agent particles enmeshed therein.

One more specific process for preparing the concentration device is a wet laying or "wetlaid" process. In this process, a dispersion is formed that contains (a) a plurality of fibers, (b) a plurality of concentration agent particles, (c) a polymeric binder, (d) and a dispersing liquid such as water, a water-miscible organic solvent, or a mixture thereof. The fibers, concentration agent particles, and polymeric binder components can be dispersed together in the dispersing liquid. Alternatively, one or two of these components can be dispersed prior to the introduction of the other components. In some embodiments, the fibers have additives, surface treatments, or chemical groups that facilitate dispersion of the fibers in the dispersion liquid. For example, polyolefin-based fibers can have maleic anhydride or succinic anhydride functionality, or, during the melt-processing to prepare polyolefin-based fibers, a suitable surfactant can be added.

The wetlaid process additionally includes at least partially depositing the polymeric binder onto at least a portion of the fibers and removing the dispersing liquid from the dispersion. Deposition of the polymeric binder onto the fibers can be carried out either before or after the dispersing liquid removal or dewatering step, depending upon the nature of the polymeric binder. For example, when a polymeric latex is used as the polymeric binder, the polymeric latex can be precipitated onto the fibers before or after concentration agent particle addition and prior to dewatering. After the dewatering, heat can be applied to finish the dewatering and to set the resulting deposited latex. When polymeric binder fibers are used as the polymeric binder, dewatering can generally be carried out first, followed by heating to finish the dewatering and to melt the polymeric binder fibers (and thereby deposit polymeric binder on the fibers).

One or more adjuvants or additives can be used in preparing this type of concentration device. Useful adjuvants include process aids (for example, precipitation agents such as sodium aluminates and aluminum sulfate, which can aid in precipitating the polymeric binder onto the fibers), materials that can enhance the overall performance of the resulting concentration device, and the like. When used, the amounts of such adjuvants can be present, for example, in an amount up 5 weight percent, up to 4 weight percent, up to 3 weight percent, up to 1 weight percent, or even up to 0.5 weight percent based on a total dry weight of the concentration device (for example, fibers, concentration agent, and polymeric binder). The total amount of adjuvants is typically selected to be as low as possible so as to maximize the amount of concentration agent particles that can be included in the concentration device.

In one more specific wetlaid process, the fibers (for example, chopped fibers) can be blended in a container in the presence of the dispersing liquid (for example, water, a water-miscible organic solvent such as an alcohol, or a mixture thereof) to form a slurry. After formation of the slurry, the concentration agent particles, the polymeric binder, and an optional precipitation agent (for example, a pH adjusting agent such as alum) can be added to the slurry.

When the wetlaid process is carried out by using handsheet methods known in the art, the order of addition of the three components (i.e., fibers, polymeric binder, and concentration agent particles) to the dispersion has not been found to significantly affect the ultimate performance of the concentration device. Addition of the polymeric binder after addition of the concentration agent particles, however, can provide a concentration device exhibiting somewhat greater adhesion of the concentration agent particles to the fibers.

After formation, the dispersion mixture can be poured into a mold, the bottom of which can be covered by a screen. The dispersing liquid can be allowed to drain from the mixture (in the form of a wet sheet) through the screen. After sufficient liquid has drained, the wet sheet generally can be removed from the mold and dried by pressing, heating, or a combination of the two. Generally pressures are in a range of about 300 to about 600 kPa. Temperatures in a range of 90° C. to 200° C., in a range of 100° C. to 175° C., in a range of 90° C. to 150° C., or even in a range of 90° C. to 120° C. can be used for drying the wet sheet. Drying often removes all or most of the dispersing liquid (for example, up to 85 weight percent, up to 90 weight percent, up to 95 weight percent, up to 98 weight percent, or even up to 99 weight percent of the dispersing liquid based on the amount of dispersing liquid added to form the dispersion). When polymeric binder fibers are used as the polymeric binder in the wetlaid process, a precipitation agent is typically not needed and the applied heat can be used to melt the polymeric binder fibers.

The resulting dry sheet can have an average thickness of at least 0.1 millimeter, at least 0.2 millimeters, at least 0.5 millimeters, at least 0.8 millimeters, at least 1 millimeter, at least 2 millimeters, at least 4 millimeters, or at least 5 millimeters. The average thickness is often up to 20 millimeters, up to 15 millimeters, up to 12 millimeters, or even up to 10 millimeters. Calendering can be used to provide additional pressing or fusing, if desired, of the dry sheet.

In the concentration devices that include a fibrous, non-woven porous matrix, the concentration agents can be entrapped through either chemical interactions (for example, chemical bonding) or physical interactions (for example, adsorption or mechanical entrapment), depending upon the nature of the fibers that are utilized.

Since the capacity and efficiency of the concentration device can vary according to the amount of concentration agent particles contained therein, relatively high particle loadings generally can be desirable. The amount of the concentration agent in the concentration device is often in a range of 10 to 90 weight percent based on a total weight of solids in the concentration device (for example, fibers, polymeric binder, and concentration agent). If less than 10 weight percent of the concentration agent is used, the effectiveness of the concentration device for concentrating microorganisms may be undesirably low. If more than 90 weight percent of the concentration agent is used, there may be too few fibers present to form a porous matrix. In some example concentration devices, the concentration agent is present in an amount equal to at least 20 weight percent, at least 30 weight percent, at least 40 weight percent, or even at least 50 weight percent based on the total weight of solids in the concentration device. The amount of concentration agent particles in the concentration device is often up to 85 weight percent, up to 80 weight percent, up to 75 weight percent, up to 70 weight percent, or even up to 60 weight percent based on the total weight of solids in the concentration device. The concentration agents are often preferably distributed essentially uniformly throughout the porous matrix.

Generally the average pore size of the dry sheet material can be in a range of 0.1 to 10 micrometers, as measured by scanning electron microscopy (SEM). Void volumes in the range of 20 to 80 volume percent or in a range of 40 to 60 volume percent can be useful. The porosity of the dry sheet materials can be modified (increased) by using fibers of larger diameter or stiffness in the fiber mixture.

The dry sheet material can be flexible (for example, it can be rolled around a 0.75 inch (about 2 cm) diameter core). This flexibility can enable the sheet material to be pleated or rolled. The sheet material can have a relatively low back pressure (i.e., a relatively high volume of liquid can be relatively quickly passed through it without generating a relatively high back pressure). As used herein, "relatively low back pressure" refers to a differential back pressure no greater than 3 pounds per square inch (20.7 kPa), no greater than 2.5 pounds per square inch (17.2 kPa), no greater than 2 pounds per square inch (13.8 kPa), no greater than 1.5 pounds per square inch (10.3 kPa), no greater than 1 pound per square inch (6.9 kPa), or no greater than 0.5 pound per square inch (3.5 kPa) at a 3 $mL/cm^2$ flowrate, wherein the flowrate is based on the frontal surface area of the sheet material.

The uncalendered sheet material can be cut to a desired size and used to bind a microorganism when contacted with a fluid sample. If desired (for example, when a significant pressure drop across the sheet is not a concern), the sheet material can be calendered to increase its tensile strength prior to use. When the sheet material is to be pleated, drying and calendering are typically avoided.

In some concentration devices with a fibrous, nonwoven porous matrix, a single layer of the dry sheet material can be effective. In other concentration devices, multiple layers of the dry sheet material are used to provide greater binding capacity for microorganisms.

Any of the above described concentration devices can further include one or more other components such as, for example, one or more pre-filters (for example, to remove relatively large particles from a sample prior to passage through the porous matrix), a manifold for applying a pressure differential across the device (for example, to aid in passing a sample through the porous matrix), and/or an external housing (for example, a disposable cartridge to contain and/or protect the porous matrix).

Any of the above described concentration devices can be contacted with a fluid sample containing a microorganism in any suitable manner. The concentration device can be added to the fluid sample, or the fluid sample can be added to the concentration device. The concentration device can be immersed in a fluid sample, a fluid sample can be poured onto the concentration device, a fluid sample can be poured into a tube or well containing the concentration device, or a sample can be passed over or through the concentration device. Preferably, the contacting is carried out in a manner such that the fluid sample passes through at least one pore of the porous matrix.

The concentration device and the fluid sample can be combined (using any order of addition) in any of a variety of containers or holders. Suitable containers or holders are typically designed to hold both the concentration device and the fluid sample without leakage. Some example containers can be capped, closed, or sealed. In some embodiments, the container or holder is a column or a syringe barrel. Suitable containers for use in carrying out the process of the invention will be determined by the particular sample and can vary widely in size and nature. For example, the container can be small, such as a 10 microliter container (for example, a test tube or syringe) or larger, such as a 100 milliliter to 3 liter container (for example, an Erlenmeyer flask or an annular cylindrical container).

The container, the concentration device, and any other apparatus or additives that contact the fluid sample directly can be sterilized (for example, by controlled heat, ethylene oxide gas, or radiation) prior to use, in order to reduce or prevent any contamination of the fluid sample that might cause detection errors. The amount of concentration agent in the concentration device that is sufficient to capture or concentrate the microorganisms of a particular fluid sample for successful detection will vary (depending upon, for example, the nature and form of the concentration agent and device and the volume of the fluid sample) and can be readily determined by one skilled in the art.

The period of contact between the concentration device and the fluid sample can be any desired amount of time. For example, the contact time can be up to 24 hours, up to 12 hours, up to 6 hours, up to 4 hours, up to 2 hours, up to 1 hour, up to 30 minutes, up to 15 minutes, up to 10 minutes, up to 5 minutes, up to 1 minute, up to 30 seconds, or even up to 15 seconds. Contact can be enhanced by mixing (for example, by stirring, by shaking, or by application of a pressure differential across the concentration device to facilitate passage of fluid a sample through its porous matrix).

In some embodiments, the fluid sample is passed at least once (often, only once) through the concentration device (for example, by pumping, pressure, or gravity feed). Essentially any type of pump (for example, a peristaltic pump) or other equipment for establishing a pressure differential across the concentration device (for example, a syringe or plunger) can be utilized. Sample flow rates through the concentration device of up to about 100 milliliters per minute or more can be effective. The flow rates can be, for example, in a range of 1 to 100 milliliters per minute, in a range of 10 to 100 milliliters/minute, in a range of 10 to 50 milliliters per minute, or even in a range of 10 to 25 milliliters per minute.

If desired, one or more optional additives can be added to the mixture of fluid sample and concentration device. Suitable additives include, but are not limited to, lysis reagents, bioluminescence assay reagents, microbial growth media, buffers (for example, to disperse or extract a solid sample), microbial staining reagents, washing buffers (for example, to wash away unbound material), elution agents (for example, serum albumin), surfactants, and mechanical abrasion/elution agents (for example, glass beads).

While the fluid sample is in contact with the concentration device, microorganisms present in the fluid sample can become bound to the concentration agent in the concentration device. The bound microorganism (i.e., the microorganisms bound to the concentration agent in the concentration device) is typically separated from the residual fluid sample. It can also be possible to isolate or separate bound microorganisms (or one or more components thereof) from the concentration device after contacting. For example, an elution agent or a lysis agent can be passed over or through the concentration device.

Any of the above described concentration devices can be used as filter media for removing microbial contaminants or pathogens from a fluid sample (for example, water). The filter media include a porous matrix and a plurality of concentration agent particles distributed on a surface of the porous matrix, distributed throughout the porous matrix, or a combination thereof. In some embodiments, the filter media contains (a) a fibrous, nonwoven porous matrix and (b) a plurality of concentration agent particles, the particles enmeshed in the porous fibrous nonwoven matrix. In other embodiments, the filter media contains (a) a porous matrix of sintered polymeric particles and (b) a plurality of concentration agent particles, the particles embedded in the porous matrix of sintered polymeric particles.

A variety of microorganisms can be concentrated and detected by using the above described concentration agents and concentration devices. Samples can contain a plurality of microorganism strains, and any one strain can be detected independently of any other strain. These microorganisms include, but are not limited to, bacteria (including gram-positive bacteria and gram-negative bacteria), fungi, molds, yeasts, protozoans, viruses (including both non-enveloped and enveloped viruses), bacterial endospores, and the like, and combinations thereof.

Genera of target microorganisms to be detected include, but are not limited to, *Listeria, Escherichia, Salmonella, Campylobacter, Clostridium, Helicobacter, Mycobacterium, Staphylococcus, Shigella, Enterococcus, Bacillus, Neisseria, Shigella, Streptococcus, Vibrio, Yersinia, Bordetella, Borrelia, Pseudomonas, Saccharomyces, Candida*, and the like, and combinations thereof.

Specific microorganism strains that can be targets for detection include *Escherichia coli, Yersinia enterocolitica, Yersinia pseudotuberculosis, Vibrio cholerae, Vibrio parahaemolyticus, Vibrio vulnificus, Listeria monocytogenes, Staphylococcus aureus, Salmonella enterica, Saccharomyces cerevisiae, Candida albicans,* Staphylococcal entero-

*toxin* ssp, *Bacillus cereus, Bacillus anthracia, Bacillus atrophaeus, Bacillus subtilis, Clostridium perfringens, Clostridium botulinum, Clostridium difficile, Enterobacter sakazakii*, human-infecting non-enveloped enteric viruses for which *Escherichia coli* bacteriophage is a surrogate, *Pseudomonas aeruginosa*, and the like, and combinations thereof.

The microorganisms typically remain viable even after being bound to the concentration agent. They are capable of replicating or reproducing upon availability of favorable conditions such as suitable nutrients.

The capture efficiency, which can also be referred to as the binding efficiency, is typically at least 50 percent, at least 60 percent, at least 70 percent, at least 80 percent, at least 90 percent, or even at least 90 percent based on the total amount of microorganisms in a sample.

Microorganisms that have been captured or bound (for example, by adsorption or by sieving) by the concentration device or concentration agent can be detected by essentially any desired method that is currently known or hereafter developed. Such methods include, for example, culture-based methods (which can be preferred when time permits), microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism capture optionally can include washing to remove sample matrix components, slicing or otherwise breaking up the porous fibrous nonwoven matrix of the concentration device, staining, boiling or using elution buffers or lysis agents to release cellular analyte from the concentration device, or the like.

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification), which is often a preferred method. The captured or bound microorganisms can be lysed to render their genetic material available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, or viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adensosine triphosphate (ATP) detection methods including those described in U.S. Pat. No. 7,422,868 (Fan et al.). Other luminescence-based detection methods can also be utilized.

Since the concentration agents and concentration devices described above are non-strain specific, they can be used to provide a general capture system that allows for multiple microorganism strains to be targeted for assay in the same sample. For example, in assaying for contamination of food samples, it can be desired to test for *Listeria monocytogenes, Escherichia coli*, and *Salmonella* all in the same sample. A single capture step can then be followed by, for example, PCR or RT-PCR assays using specific primers to amplify different nucleic acid sequences from each of these microorganism strains. Thus, the need for separate sample handling and preparation procedures for each strain can be avoided.

A diagnostic kit can be provided that includes (a) at least one above-described concentration device or concentration agent; and (b) at least one testing container or testing reagent (preferably, a sterile testing container or testing reagent) for use in carrying out the concentration process of the invention. Preferably, the diagnostic kit further comprises instructions for carrying out the process.

Useful testing containers or holders include those described above and can be used, for example, for contacting, for incubation, for collection of eluate, or for other desired process steps. Useful testing reagents include microorganism culture or growth media, lysis agents, elution agents, buffers, luminescence detection assay components (for example, luminometer, lysis reagents, luciferase enzyme, enzyme substrate, reaction buffers, and the like), genetic detection assay components, and the like, and combinations thereof. A preferred lysis agent is a lytic enzyme or chemical supplied in a buffer, and preferred genetic detection assay components include one or more primers specific for a target microorganism. The kit can optionally further include sterile forceps or the like.

Various items are provided that are processes for concentrating a microorganism or articles that include a concentration agent for microorganisms.

Item 1. A process for concentrating a microorganism, the process comprising:
  (a) providing a concentration agent comprising a bismuth-containing material, wherein the bismuth-containing material is any of bismuth oxide, bismuth carbonate, bismuth oxycarbonate, bismuth oxychloride, or a mixture thereof;
  (b) providing a fluid sample comprising the microorganism;
  (c) contacting the concentration agent with the fluid sample; and
  (d) binding the microorganism to the concentration agent to form a bound microorganism, wherein the bound microorganism is living.

Item 2. The process of item 1, wherein the concentration agent comprises particles.

Item 3. The process of any of items 1 to 2, wherein the microorganism is a strain of bacteria, fungi, yeast, protozoan, virus, bacterial endospore, or a mixture thereof.

Item 4. The process of item 1 to 3, wherein the microorganism is gram-negative bacteria or gram-positive bacteria.

Item 5. The process of any one of items 1 to 4, further comprising segregating the bound microorganism from the fluid sample.

Item 6. The process of any of items 1 to 5, wherein the concentration agent comprises a plurality of particles and further comprises a porous matrix, wherein the plurality of particles are distributed on a surface of the porous matrix, distributed throughout the porous matrix, or distributed both on the surface and throughout the porous matrix.

Item 7. The process of item 6, wherein the porous matrix comprises nonwoven fibers.

Item 8. The process of item 7, wherein the nonwoven fibers comprise fibrillated fibers.

Item 9. The process of item 7, wherein the nonwoven fibers are polymeric fibers, inorganic fibers, or a combination thereof.

Item 10. The process of any one of items 6 to 9, wherein the porous matrix further comprises a polymeric binder.

Item 11. The process of item 6, wherein the porous matrix comprises a sintered polymeric material.

Item 12. The process of item 11, sintered polymeric material is a sintered thermoplastic polymer.

Item 13. The process of any one of items 1 to 12, further comprising detecting the presence of the bound microorganism.

Item 14. An article comprising:
  a concentration agent comprising a bismuth-containing material, wherein the bismuth-containing material is any of bismuth oxide, bismuth carbonate, bismuth oxycarbonate, bismuth oxychloride, or a mixture thereof;
  a microorganism bound to the concentration agent,
  wherein the microorganism is living.

Item 15. The article of item 14, wherein the concentration agent comprises a plurality of particles.

Item 16. An article comprising:
  a concentration agent comprising a bismuth-containing material, wherein the bismuth-containing material is any of bismuth oxide, bismuth carbonate, bismuth oxycarbonate, bismuth oxychloride, or a mixture thereof; and
  a porous matrix, wherein the concentration agent is distributed on a surface of the porous matrix, throughout the porous matrix, or a combination thereof.

Item 17. The article of item 16, wherein the concentration agent comprises a plurality of particles.

Item 18. The article of any one of items 16 to 17, wherein the porous matrix comprises nonwoven fibers and an optional polymeric binder.

Item 19. The article of item 18, wherein the nonwoven fibers comprise polymeric fibers, inorganic fibers, or a combination thereof.

Item 20. The article of any one of items 16 to 17, wherein the porous matrix comprises a sintered polymeric material.

Item 21. The article of item 20, wherein the sintered polymeric material comprises a sintered thermoplastic material.

Item 22. The article of any one of items 16 to 21, wherein the porous matrix is in the form of filter media.

Item 23. The article of any one of items 16 to 22, further comprising a microorganism bound to the concentration agent.

Item 24. The process of any one of items item 1 to 13, wherein the concentration agent is bismuth oxide.

Item 25. The process of any one of items item 1 to 13, wherein the concentration agent is bismuth carbonate.

Item 26. The process of any one of items item 1 to 13, wherein the concentration agent is bismuth oxycarbonate.

Item 27. The process of any one of items item 1 to 13, wherein the concentration agent is bismuth oxychloride.

Item 28. The process of any one of items 1 to 13, wherein the bismuth-containing material is anhydrous.

Item 29. The process of any one of items 1 to 13, wherein the bismuth containing material is at least partially hydrated.

Item 30. The article of any one of items item 14 to 15, wherein the concentration agent is bismuth oxide.

Item 31. The article of any one of items item 14 to 15, wherein the concentration agent is bismuth carbonate.

Item 32. The article of any one of items item 14 to 15, wherein the concentration agent is bismuth oxycarbonate.

Item 33. The article of any one of items item 14 to 15, wherein the concentration agent is bismuth oxychloride.

Item 34. The article of any one of items 14 to 15, wherein the bismuth-containing material is anhydrous.

Item 35. The article of any one of items 14 to 15, wherein the bismuth containing material is at least partially hydrated.

Item 36. The article of any one of items item 16 to 22, wherein the concentration agent is bismuth oxide.

Item 37. The article of any one of items item 16 to 22, wherein the concentration agent is bismuth carbonate.

Item 38. The article of any one of items item 16 to 22, wherein the concentration agent is bismuth oxycarbonate.

Item 39. The article of any one of items item 16 to 22, wherein the concentration agent is bismuth oxychloride.

Item 40. The article of any one of items 16 to 22, wherein the bismuth-containing material is anhydrous.

Item 41. The article of any one of items 16 to 22, wherein the bismuth containing material is at least partially hydrated.

Item 42. A kit comprising:
  (a) a concentration agent that comprises:
    a bismuth-containing material, wherein the bismuth-containing material is any of bismuth oxide, bismuth carbonate, bismuth oxycarbonate, bismuth oxychloride, or a mixture thereof; and
    a porous matrix, wherein the concentration agent is distributed on a surface of the porous matrix, throughout the porous matrix, or a combination thereof;
  (b) a testing container; and
  (c) instructions for using said concentration agent in carrying out the process of item 6.

EXAMPLES

As used in the examples, all percentages are by weight unless otherwise specified. All of the examples were tested in duplicate unless indicated otherwise. Unless otherwise specified, all materials were used as received.

Materials

| | |
|---|---|
| AC plate | aerobic count detection plate, obtained from 3M Company, St. Paul, MN, under the trade designation "3M AEROBIC COUNT PETRIFILM PLATE" |
| Adsorption buffer | pH 7.2, 100X strength buffer containing 5 millimoles KCl, 1 millimole $CaCl_2$, 0.1 millimole $MgCl_2$, and 1 millimole $K_2HPO_4$, prepared in DI water |
| BHI Broth | bovine heart infusion broth obtained from Becton Dickinson, Sparks, MD, under the trade designation "DIFCO BOVINE HEART INFUSION BROTH", prepared at 3.7% concentration according to the manufacturer's instructions |
| Bismuth carbonate | bismuth carbonate powder, obtained from Pfaltz & Bauer, Inc., Stamford, CT. The commercially obtained bismuth carbonate contained predominately $Bi_2O_2CO_3$ (bismuthite, alternatively referred to as bismuth subcarbonate or bismuth oxycarbonate; PDF: 04-009-8533), according to X-ray diffraction analysis. |
| Bismuth oxychloride | bismuth oxychloride (BiOCl) powder, obtained from Alfa Inorganics Ventron, Beverly, MA |
| Bismuth subsalicylate | bismuth subsalicylate U.S.P. grade powder, obtained from Mallinckrodt, St. Louis, MO |
| Butterfield's buffer | pH 7.2 ± 0.2, monobasic potassium phosphate buffer solution, obtained from VWR, West Chester, PA (VWR Catalog Number 83008-093) |
| DI water | deionized, filtered, 18 megaohm water, processed through Milli-Q Gradient System obtained from Millipore; Waltham, MA |
| E. coli plate | E. coli detection plate obtained 3M Company, St. Paul, MN, under the trade designation "3M E COLI/COLIFORM PETRIFILM PLATE" |
| Fiber 1 | 1 denier fibrillated polyethylene fibers, obtained from Minifibers, Inc., Johnson City, TN, under the trade designation "FYBREL600" |
| Fiber 2 | 6 denier 2 inches long chopped nylon fibers, obtained from Minifibers, Inc. |
| Fiber 3 | 1 denier bicomponent ethylene vinyl acetate/polypropylene fibers, obtained from Minifibers, Inc. |
| Fiber 4 | long glass fibers, obtained from Schuller, Inc., Denver, CO, under the trade designation "MICRO-STRAND 106-475 GLASS FIBERGLAS" |
| Filter holder | 13 mm diameter filter holder obtained from Millipore Corp., Bedford, MA, under the trade designation "SWINNEX FILTER HOLDER" |
| Flocculant | flocculant agent obtained from Midsouth Chemical Co., Inc., Ringgold, LA, under the trade designation "9307 FLOCCULANT" |
| Latex binder | 50% solids vinyl acetate emulsion, obtained from Air Products Polymers, Allentown, PA, under the trade designation "AIRFLEX 600BP" |
| MOX plate | plate with Oxford Medium, modified for Listeria, obtained from Hardy Diagnostics, Santa Maria, CA |
| Stomacher | laboratory blender, obtained from VWR under the trade designation "STOMACHER 400 CIRCULATOR LABORATORY BLENDER" |
| Stomacher bags | polyethylene sample bags, obtained from VWR under the trade designation "FILTRA-BAG" (vwr CATALOG #89085-574) |
| Syringe | plastic syringe obtained from VWR under the trade designation "BD LUER-LOK TIP" |
| Tryptic Soy Agar plate | plate with DIFCO Tryptic Soy Agar obtained from BD, Sparks, MD, prepared at 3% according to the manufacturer's instructions |
| YM plate | yeast and mold detection plate, obtained from 3M Company, St. Paul, MN, under the trade designation "3M PETRIFILM YEAST AND MOLD PLATE" |
| YPD agar plate | agar plate prepared according to manufacturer's instructions with 5% Yeast Extract Peptone Dextrose and 1.5% agar, both powders from BD |
| 0.5 McFarland Standard | McFarland standards are used as a reference to adjust the turbidity of bacterial suspensions so that the number of bacteria will be within a given range. A 0.5 Mc Farland number corresponds to bacterial concentration of about $1-1.5 \times 10^8$ CFU/mL. Turbidity was adjusted using a densitometer (obtained from bioMerieux, Inc., Durham, NC, under the trade designation "DENSICHECK") |

Bacterial and Yeast Cultures

Escherichia coli (ATCC 51813), Staphylococcus aureus (ATCC 6538), Pseudomonas aeruginosa (ATCC 9027) Saccharomyces cerevisiae (ATCC 201390), and Listeria monocytogenes (ATCC 51414) were purchased from American Type Culture Collection, Manassas, Va., unless stated otherwise. Unless otherwise specified, bacteria for testing were isolated from a streak culture prepared by streaking the culture on a Tryptic Soy Agar plate and incubating overnight at 37° C. according to standard microbiology practices. Yeast cultures for testing were isolated from streak culture prepared by streaking the culture on a Yeast Extract Peptone Dextrose Agar plate and incubating overnight at 30° C. according to standard microbiology practices.

Colony Count

Colonies were counted manually according to standard microbiology procedures unless otherwise stated.

X-Ray Diffraction Analysis

Samples were examined directly on a zero background quartz insert. Reflection geometry data were collected in the form of a survey scan using a Philips vertical diffractometer, copper $K_\alpha$ radiation, and proportional detector registry of the scattered radiation. The diffractometer was fitted with variable incident beam slits, fixed diffracted beam slits, and a graphite diffracted beam monochromator. The survey scan was conducted from 5 to 80 degrees (2θ) using a 0.04 degree step size and 4 second dwell time. The X-ray generator was set at 45 kV and 35 mA. Powder diffraction files (PDF) were used for identification of phases based on the reflections observed in the diffraction patterns.

Preparation of Bismuth Oxide

Commercially obtained bismuth carbonate (34.36 g) was heated in a quartz boat from 22° C. to 450° C. in 60 minutes and held at 450° C. for 120 minutes before slowly cooling to ~50° C. All heating was performed in air in a box furnace (obtained from Carbolite LTD, Hope Valley, UK, under the trade designation "CARBOLITE RHF 1500 FURNACE"). The resulting powder was bright yellow in color and weighed 31.58 g. X-ray diffraction analysis of the product showed the presence of predominantly bismuth oxide ($Bi_2O_3$, PDF: 01-074-1374) with a minor amount of bismuthite ($Bi_2O_2CO_3$, PDF: 04-009-8533; the commercially obtained bismuth carbonate contains predominately bismuthite, according to X-ray diffraction analysis).

Capture of E. coli on Concentration Agents

E. coli Microorganism Suspension

A streak culture of Escherichia coli (E. coli), a Gram negative bacterium, was used to prepare a 0.5 McFarland Standard in 3 mL of DI Water. The resulting bacterial stock, containing $10^8$ colony forming units per milliliter ("CFU/ml"), was serially diluted in an Adsorption buffer to obtain a bacterial suspension having $10^3$ microorganisms per mL suspension ("E. coli microorganism suspension"), which was used in making the following samples.

EC-1

A 1.0 mL volume of the E. coli microorganism suspension was added to a labeled, sterile 5 mL polypropylene tube (obtained from Becton Dickinson, Franklin Lakes, N.J., under the trade designation "BD FALCON") containing 10 milligrams of the bismuth oxide prepared above.

EC-2

A 1.0 mL volume of the *E. coli* microorganism suspension was added to a labeled, sterile 5 mL polypropylene tube ("BD FALCON") containing 10 milligrams of bismuth carbonate.

EC-3

A 1.0 mL volume of the *E. coli* microorganism suspension was added to a labeled, sterile 5 mL polypropylene tube ("BD FALCON") containing 10 milligrams of bismuth oxychloride.

EC-4 (Comparative)

A 1.0 mL volume of the *E. coli* microorganism suspension was added to a labeled, sterile 5 mL polypropylene tube ("BD FALCON") containing 10 milligrams of bismuth subsalicylate.

An *E. coli* control sample was prepared by adding a 1.0 mL volume of the *E. coli* microorganism suspension to a labeled, sterile 5 mL polypropylene tube ("BD FALCON"), without the addition of any concentration agent.

Processing of *E. coli* Samples

The tubes containing samples EC-1 to EC-4 and the *E. coli* control sample described above were capped and mixed on a vortex mixer (obtained from Barnstead International, Dubuque, Iowa, under the trade designation "THERMOLYNE MAXIMIX PLUS VORTEX MIXER") and agitated at room temperature (25° C.) for 10 minutes at 14 cycle/minute on a platform rocker (obtained from Barnstead International, under the trade designation "THERMOLYNE VARI MIX PLATFORM ROCKER"). After the agitation, each tube was allowed to stand on a lab bench for 10 minutes, allowing the any powders present to settle.

For each tube, the settled materials were collected and re-suspended in 1 mL of sterile Butterfield's buffer for plating on AC plates according to the manufacturer's instructions. The *E. coli* control sample was also plated on AC plates. The plates were incubated at 37° C. for 18-20 hours. Colony counts were determined using a plate reader (obtained from 3M Company, St. Paul, Minn., under the trade designation "3M PETRIFILM PLATE READER").

The Capture Efficiency (Efficiency) was equal to the number, in percent, of the microorganisms that were captured on the re-suspended material. The Capture Efficiency was determined from the number of colonies counted from the re-suspended material ("Captured") and the number of colonies counted from the untreated control sample ("Control") according to the following formula:

Capture Efficiency (%)=((Captured)/(Control))×100

The Capture Efficiency results for the *E. coli* samples are shown in Table 1.

TABLE 1

| Example | Sample | Concentration Agent | Capture Efficiency (%) |
|---------|--------|---------------------|------------------------|
| 1 | EC-1 | bismuth oxide | 85 |
| 2 | EC-2 | bismuth carbonate | 88 |
| 3 | EC-3 | bismuth oxychloride | 92 |
| C1 | EC-4 | bismuth subsalicylate | 0 |

Standard deviation in Capture Efficiency is less than 10% unless noted otherwise. The control sample for data in Table 1 contained 130 CFU/mL *E. coli*. For the bismuth subsalicylate sample EC-4 (comparative example C1), no colony counts were obtained from the plated settled material or supernatant.

Capture of *S. aureus* on Concentration Agents

Samples were prepared and tested according to the procedure described above for *E. coli*, except that the organism tested was *Staphylococcus aureus* (*S. aureus*), a Gram positive bacterium. Accordingly, samples SA-1, SA-2, and SA-3 included *S. aureus* and the Concentration Agents indicated in Table 2. Capture Efficiency results are shown in Table 2.

TABLE 2

| Example | Sample | Concentration Agent | Capture Efficiency (%) |
|---------|--------|---------------------|------------------------|
| 4 | SA-1 | bismuth oxide | 100 |
| 5 | SA-2 | bismuth carbonate | 99 |
| 6 | SA-3 | bismuth oxychloride | 100 |

The control sample for data in Table 2 contained 39 CFU/mL *S. aureus*.

Capture of *P. Aeruginosa* on Concentration Agents

Samples were prepared and tested according to the procedure described above for *E. coli*, except that the organism tested was *Pseudomonas aeruginosa* (*P. aeruginosa*), a Gram negative bacterium. Accordingly, samples PA-1, PA-2, PA-3, and PA-4 included *P. aeruginosa* and the Concentration Agents indicated in Table 3. Capture Efficiency results are shown in Table 3.

TABLE 3

| Example | Sample | Concentration Agent | Capture Efficiency (%) |
|---------|--------|---------------------|------------------------|
| 7 | PA-1 | bismuth oxide | 47 |
| 8 | PA-2 | bismuth carbonate | 44 |
| 9 | PA-3 | bismuth oxychloride | 41 |
| C2 | PA-4 | bismuth subsalicylate | 0 |

The control sample for data in Table 3 contained 49 CFU/mL *P. aeruginosa*. For the bismuth subsalicylate sample PA-4 (comparative example C2), no colony counts were obtained from the plated settled material or supernatant.

Preparation of Porous Matrices that Include a Concentration Agent

Example 10

A fiber premix was prepared by mixing 30.0 g of Fiber 1, 6.0 g of Fiber 2, 4.5 g of Fiber 3, and 3.0 g of Fiber 4 with 4 liters of cold tap water in a 4 L blender (available from VWR, Radnor, Pa., under the trade designation "WARING COMMERCIAL HEAVY DUTY BLENDER, MODEL 37BL84") at medium speed for 60 seconds. The mixture was examined for uniform dispersion of the fibers without nits or clumps, and blended further as needed to break up clumps. One liter of the fiber premix was added to a 1 liter stainless steel beaker and mixed with an impeller mixer (obtained from ThermoFisher Scientific, Waltham, Mass., under the trade designation "STEDFAST STIRRER MODEL SL2400") at a speed setting of 4 for five minutes. Then 0.5 g of latex binder was dispersed in about 25 mL of tap water in a 50 mL beaker and added to the mixture. The beaker was rinsed with about another 25 mL of tap water that was added to the mixture and mixed for about 2 minutes. In the same manner, 1.0 g of flocculant was dispersed in about 25 mL of tap water and added to the mixture while mixing, followed by the addition of about another 25 mL of rinse water from the beaker. The latex binder crashed out of solution onto the fibers and the liquid phase of the premix changed from cloudy to substantially clear. Then a 5.0 gram portion of the bismuth oxide (prepared above) was added and mixed on a vortex mixer for 1 minute.

A felt was prepared using a pad maker apparatus (obtained from Williams Apparatus, Watertown, N.Y., under the trade designation "TAPPI") that had a box measuring about 20 centimeters (8 inches) square and 20 centimeters (8 inches) high with a fine mesh screen at the bottom and a drain valve. The box was filled with tap water up to a height of about 1 centimeter above the screen. The particle-containing mixture was poured into the box and the valve was opened immediately which created a vacuum that pulled the water out of the box. The resulting wetlaid felt was approximately 3 millimeters thick.

The wetlaid felt was transferred from the apparatus onto a 20 centimeter square sheet of blotter paper (96-pound white paper, obtained from Anchor Paper, St. Paul, Minn.). The felt was sandwiched between 2 to 4 layers of blotter paper, depending on the wetness of the sheet, and pressed between 2 reinforced screens in an air powered press set at 60 pounds per square inch (calculated to be about 12 pounds per square inch pressure exerted on the felt) for 1 to 2 minutes until no further water was observed being expelled. The pressed felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 120° C. for about 40 minutes to remove residual water and cure the latex binder to form a porous matrix.

Example 11

A porous matrix was prepared according to the procedure described for Example 10, except that the amount of bismuth oxide was a 10.0 g portion.

Capture of *Listeria Monocytogenes* on Porous Matrices

A streak culture of *L. monocytogenes* was used to prepare a 0.5 McFarland Standard in 3 mL of BHI Broth. The resulting bacterial stock, containing approximately $10^8$ CFU/mL, was serially diluted in BHI broth to obtain a bacterial suspension having approximately $10^3$ CFU/mL.

Filtration for Example 12

A 14 mm diameter disc was die-punched from the porous matrix of Example 10 and inserted into a filter holder (SWINNEX). A 3 mL syringe was used to deliver 1.5 mL of the bacterial suspension onto the porous matrix in the holder. The filter holder was held over a container to collect the filtrate. The filtration was completed in about 15 seconds.

Filtration for Example 13

The procedure as described in Example 12 was repeated, except that the 14 mm diameter disc was die-punched from the porous matrix of Example 11.

A 100 microliter volume from each filtrate obtained for Examples 12 and 13 was plated on MOX plates. A control sample was prepared by plating 100 microliters of the unfiltered bacterial suspension on a MOX plate. The porous matrices from Examples 12 and 13 were removed from the filter holder after each filtration using surface sterilized forceps and placed on MOX plates with 100 microliters of Butterfield's buffer. All of the plates were incubated at 37° C. for 18-20 hours. Colonies were counted manually.

The control sample had 3370 CFU/mL (5055 CFU in 1.5 mL). All of the plated discs showed growth of *L. monocytogenes* indicating that the captured bacterial cells were viable.

Colony counts from plated filtrates were used to calculate the Capture Efficiency for the porous matrices as follows. Filtration Efficiency (Efficiency) was determined from the number of colonies counted from the filtrates (Filtrate Count) and the number of colonies counted from the unfiltered control sample (Control Count) according to the following formula:

Filtration Efficiency (%)=((Filtrate Count)/(Control Count))×100

Capture Efficiency (%)=100−Filtration Efficiency

Capture Efficiency Results are shown in Table 4.

TABLE 4

| Example | Porous matrix | Capture Efficiency (%) |
|---|---|---|
| 12 | Example 10 | 65 |
| 13 | Example 11 | 85 |

Capture of *E. coli* on Porous Matrices

A streak culture of *E. coli* was used to prepare a 0.5 McFarland Standard in 3 mL of sterile DI water. The resulting bacterial stock containing $1\times10^8$ CFU/mL was serially diluted in DI water to obtain a bacterial suspension having approximately $10^5$ CFU/mL.

Example 14

A 14 mm diameter disk was die-punched from the porous matrix of Example 10 and inserted into a filter holder (SWINNEX).

Example 15

A 14 mm diameter disk was die-punched from the porous matrix of Example 11 and inserted into a filter holder (SWINNEX).

A 3 mL syringe was used to deliver 1.0 mL of the bacterial suspension onto the matrix in the filter. After filtering, the filtrate was collected, diluted 1:100 in DI water, and plated on *E. coli* plates. A Control sample was prepared by diluting the bacterial suspension having approximately $10^5$ CFU/mL 1:100 in Butterfield's buffer and plating 1 mL of the dilution. The plates were incubated at 37° C. for 18-20 hours. Colony counts were determined using a plate reader (obtained from 3M Company, St. Paul, Minn., under the trade designation "3M PETRIFILM PLATE READER").

The Log Reduction Value ("LRV") is an indication of bacterial removal capacity of a filtration matrix. The values were calculated based on the log value of the colony count (CFU/mL) in the control (Log Control Count) less the log value of colony count in the filtrate (Filtrate Count) according to the formula:

LRV=(Log$_{10}$(Control Count))−(Log$_{10}$(Filtrate Count))

The Control had an average colony count of 135,000 CFU/mL (5.13 Log CFU/mL). Log Reduction Values for Examples 14 and 15 are shown in Table 5.

TABLE 5

| Example | Porous matrix | LRV |
|---------|---------------|------|
| 14 | Example 10 | 2.23 |
| 15 | Example 11 | 4.03 |

Capture of S. cerevisiae (from a Beer Sample) on a Porous Matrix

A streak culture of Saccharomyces cerevisiae (S. cerevisiae) from a YPD agar plate was used to make a 0.5 McFarland Standard in 3 mL of beer ("MICHELOB GOLDEN LIGHT Draft" beer with 4.3% alcohol, purchased from a local retail store). The resulting yeast stock, containing approximately $10^6$ CFU/mL, was diluted serially in beer to obtain a yeast suspension containing $10^3$ CFU/mL. A spiked beer sample was prepared with a 1:100 dilution of the suspension inoculated into 100 mL of beer to provide 10 CFU/mL.

A 14 mm disc was die-punched from the porous matrix of Example 11 and inserted into a filter holder (SWINNEX). The spiked beer sample (100 mL) was delivered to the filter holder in five batches using a 20 mL syringe. After the entire sample passed through the matrix, the disc was transferred, using surface sterilized forceps, to an empty sterile 1.5 mL polypropylene microcentrifuge tube (VWR, Catalog #89000-028).

Example 16

Concentration of Yeast Microorganisms from a Beer Sample

A "Concentrated Sample Disc" was prepared by adding 100 microliters of an enzyme solution and 50 microliters of an extractant solution from a sample preparation kit (obtained from 3M Company; St. Paul, Minn., under the trade designation "3M CLEAN-TRACE SURFACE ATP SYSTEM") to the tube containing the disc as described above. The contents were mixed for 5 seconds at about 3200 rpm on a vortex mixer (obtained from VWR, West Chester Pa., under the trade designation "VWR FIXED SPEED VORTEX MIXER"). The ATP signal of the sample was measured in relative light units (RLU) for one minute at 10 second intervals using a bench-top luminometer (obtained from Turner Biosystems, Sunnyvale, Calif., under the trade designation "20/20N SINGLE TUBE LUMINOMETER", equipped with 20/20n SIS software). Luminescence values were analyzed as described below. Direct detection of ATP was done without need for prior extraction/elution of the captured microorganism.

The background ATP level was determined by filtering 100 mL of unspiked beer (i.e., the beer without any S. cerevisiae added) through a disc die-cut from the porous matrix of Example 11. The disc ("Unspiked Beer Background Disc") was processed according to the procedure described above for the Concentrated Sample and the ATP signal was measured.

The ATP signal for 100 microliters of only the beer ("Unspiked Beer Background") was also measured. "Unspiked Beer" refers to the beer without any addition of S. cerevisiae. The background ATP signals were subtracted from the ATP signals of the beer containing test samples to calculate the Corrected ATP Signal values as shown in Table 6.

The ATP signals were also measured for the unfiltered yeast suspension containing $10^3$ CFU (100 microliters), and the unfiltered spiked beer sample (100 microliters). These samples were used as a "$10^3$ CFU Control" and "Spiked Beer Control" samples, respectively.

The % ATP signal was calculated from the Corrected ATP Signal values for the controls according to the following equation:

% ATP Signal=(Corrected RLU/RLU from $10^3$ CFU Control)×100

Results are shown in Table 6.

TABLE 6

| Sample | ATP Signal (RLU) | Corrected ATP Signal (RLU) | % ATP Signal of $10^3$ CFU control |
|--------|------------------|---------------------------|-----------------------------------|
| Unspiked Beer Background | 3141 | | |
| Unspiked Beer Background Disc | 1300 | | |
| $10^3$ CFU Control | 3289 | 148 | 100% |
| Spiked Beer Control | 2904 | | |
| Concentrated Sample Disc | 1436 | 136 | 92% |

Yeast counts for the beer samples were determined by plating 1 mL of the 100 mL Spiked Beer Control on Y/M plates according to the manufacturer's instructions and the sample had a total of 1700 CFU of yeast cells. The data in Table 6 showed the ability of the porous matrix of Example 11 (see, e.g., Concentrated Sample Disc data) to manually process a large volume of a beverage sample and concentrate the sample from an initial 100 mL volume to a final 100 microliter volume. Direct detection of ATP was done using the porous matrices without need for prior extraction/elution of captured signal.

Examples 17 and 18

Filtration of Beef Sample Through Porous Matrices

Example 17 was prepared as follows. A ground beef sample was prepared by adding 99 mL of Butterfield's buffer and 11 grams of ground beef (15% fat), purchased from a local grocery store, to a stomacher bag and processing on a stomacher according to the manufacturer's instructions at a speed of 230 rpm for 30 seconds. A 10 mL sample was delivered with a 10 mL syringe to a 14 mm disc of Example 10 in a filter holder (SWINNEX). The syringe fit into the inlet port of the filter holder and the plunger of the syringe was used to apply positive pressure to the sample until the entire sample passed through the matrix.

Example 18 and Comparative Example C3 were prepared and tested in the same manner as described above except that Example 17 used a disc from Example 11, and Comparative Example C3 used a commercially sold 0.22 micron polycarbonate ("PC") Whatman filter (obtained from VWR) die punched to obtain a disc of 14 mm diameter.

The filtrate volumes and filtration times for Examples 17, 18, and Comparative Example C3 are shown in Table 7.

TABLE 7

| Example | Porous matrix | Filtered Volume (mL) | Filtration Time (sec) |
|---------|---------------|----------------------|------------------------|
| 17 | Example 10 | 10 | 12 |
| 18 | Example 11 | 10 | 13 |
| C3 | PC filter | 0 | 30 |

Data from Table 7 showed that the porous matrices of Examples 10 and 11 were somewhat less prone to clogging than a standard microbiology filter (polycarbonate filter) and also had greater filtration capacity when processing complex sample matrices.

Examples 19 and 20

Filtration of Soymilk Samples Through Porous Matrices

Example 19 was prepared as follows. A soymilk sample was prepared by swirling 11 mL of soymilk (4.5 grams fat), purchased from a local grocery store, with 99 mL of Butterfield's buffer. A 10 mL sample was delivered with a 10 mL syringe to a 14 mm disc of Example 10 in a filter holder (SWINNEX). The syringe fit into the inlet port of the filter holder and the plunger of the syringe was used to apply positive pressure to the sample until the entire sample passed through the matrix.

Example 20 and Comparative Example C4 were prepared and tested in the same manner as described above for Example 19, except that Example 20 used a disc from Example 11, and Comparative Example C4 used a commercially sold 0.22 micron polycarbonate (PC) Whatman filter (obtained from VWR) which was also 14 mm in diameter.

The filtrate volumes and filtration times for Examples 19, 20, and comparative example C4 are shown in Table 8.

TABLE 8

| Example | Porous matrix | Soymilk Filtered Volume (mL) | Filtration Time (sec) |
|---|---|---|---|
| 19 | Example 10 | 6 | 40 |
| 20 | Example 11 | 10 | 45 |
| C4 | PC filter | 0 | 30 |

Data from Table 8 showed that the porous matrices of Examples 10 and 11 were somewhat less prone to clogging than a standard microbiology filter (polycarbonate filter) and also had greater filtration capacity when processing complex sample matrices.

What is claimed is:

1. A process for concentrating a microorganism, the process comprising:
   (a) providing a concentration agent comprising a bismuth-containing material, wherein the bismuth-containing material is any of bismuth oxide, bismuth carbonate, bismuth oxycarbonate, bismuth oxychloride, or a mixture thereof, wherein the bismuth-containing material is in the form of a plurality of particles, and wherein the particles have an average diameter greater than 5 micrometers;
   (b) providing a fluid sample comprising the microorganism;
   (c) contacting the concentration agent with the fluid sample; and
   (d) binding the microorganism to the concentration agent to form a bound microorganism, wherein the bound microorganism is viable.

2. The process of claim 1, wherein the microorganism is a strain of bacteria, fungi, yeast, protozoan, virus, bacterial endospore, or a mixture thereof.

3. The process of claim 1, wherein the concentration agent further comprises a porous matrix, wherein the plurality of particles is distributed on a surface of the porous matrix, distributed throughout the porous matrix, or distributed both on the surface and throughout the porous matrix.

4. The process of claim 3, wherein the porous matrix comprises nonwoven fibers.

5. The process of claim 4, wherein the porous matrix further comprises a polymeric binder.

6. The process of claim 3, wherein the porous matrix comprises a sintered polymeric material.

7. An article comprising:
   a concentration agent comprising a bismuth-containing material, wherein the bismuth-containing material is any of bismuth oxide, bismuth carbonate, bismuth oxycarbonate, bismuth oxychloride, or a mixture thereof, wherein the bismuth-containing material is in the form of a plurality of particles, and wherein the particles have an average diameter greater than 5 micrometers; and
   a microorganism bound to the concentration agent, wherein the bound microorganism is viable.

8. An article comprising:
   a concentration agent comprising at least one bismuth-containing material, wherein each of the at least one bismuth-containing materials is bismuth oxide, bismuth carbonate, bismuth oxycarbonate, or bismuth oxychloride, wherein the bismuth-containing material is in the form of a plurality of particles, and wherein the particles have an average diameter greater than 5 micrometers;
   a porous matrix, wherein the concentration agent is distributed on a surface of the porous matrix, throughout the porous matrix, or a combination thereof, wherein the porous matrix comprises nonwoven fibers and an optional polymeric binder; and
   a microorganism bound to the concentration agent, wherein the bound microorganism is viable.

9. The article of claim 8, wherein the nonwoven fibers comprise polymeric fibers, inorganic fibers, or a combination thereof.

10. The process of claim 1, further comprising detecting the presence of the bound microorganism, wherein the detecting is performed in the presence of at least a portion of the concentration agent.

11. The process of claim 1, wherein the particles have an average diameter no greater than 100 micrometers.

* * * * *